United States Patent [19]

Verde Casanova et al.

[11] Patent Number: 4,722,931
[45] Date of Patent: Feb. 2, 1988

[54] CALCIUM ANTAGONIST

[75] Inventors: Maria J. Verde Casanova; Joaquin A. Galiano Ramos, both of Madrid, Spain

[73] Assignee: Laboratorios Delagrange, Madrid, Spain

[21] Appl. No.: 875,324

[22] Filed: Jun. 17, 1986

Related U.S. Application Data

[63] Continuation of Ser. No. 716,669, Mar. 27, 1985, abandoned.

[30] Foreign Application Priority Data

Mar. 27, 1984 [ES] Spain ........................... 531033
Oct. 4, 1984 [ES] Spain ........................... 536537

[51] Int. Cl.⁴ ............... C07D 491/056; C07D 211/90; A61K 31/455
[52] U.S. Cl. .................... 514/338; 514/333; 546/270; 546/256; 546/321
[58] Field of Search ............ 546/270, 321, 256; 514/333, 338

[56] References Cited

U.S. PATENT DOCUMENTS

| | | | |
|---|---|---|---|
| 3,441,648 | 4/1969 | Loev et al. | 546/321 |
| 3,775,422 | 11/1973 | Bossert et al. | 546/321 |
| 3,799,934 | 3/1974 | Meyer et al. | 546/321 |
| 3,932,645 | 1/1976 | Meyer et al. | 546/321 |
| 3,985,758 | 10/1976 | Murakami et al. | 546/321 |
| 4,031,104 | 6/1977 | Bossert et al. | 546/321 |
| 4,048,178 | 9/1977 | Gordon | 546/97 |
| 4,219,653 | 8/1980 | Kastron et al. | 546/321 |
| 4,258,042 | 3/1981 | Loev et al. | 544/122 |
| 4,264,611 | 4/1981 | Berntsson et al. | 546/321 |
| 4,284,634 | 8/1981 | Sato | 546/286 |
| 4,338,322 | 6/1982 | Sato | 546/321 |
| 4,370,334 | 1/1983 | Sato | 546/321 |
| 4,380,547 | 4/1983 | Materae | 546/270 |
| 4,510,310 | 4/1985 | Wehinger et al. | 546/270 |

FOREIGN PATENT DOCUMENTS 150 1/1979 European Pat. Off. .
7849M 6/1970 France .

OTHER PUBLICATIONS

Bossert, F., H. Meyer, and E. Wehinger, 4-Aryldihydropyridines, a New Class of Highly Active Calcium Antagonists Angew, Chem. Int. E.D. Engl. 20 (1981) 762–769.
Yakugaku Zasshi, 86:9, pp. 815–822 (1966).
J. Chem. Soc. (c) p. 138 (1969).
Synthesis, p. 761 (Sep. 1983).

Primary Examiner—Henry R. Jiles
Assistant Examiner—Dale A. Bjorkman
Attorney, Agent, or Firm—Arnold, White & Durkee

[57] ABSTRACT

The invention concerns a compound of the formula

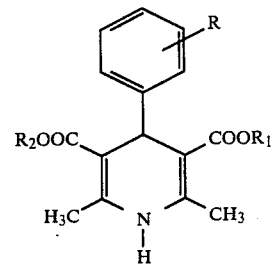

and salts thereof resulting from addition with pharmaceutically acceptable mineral or organic acid, wherein R is an alkylenedioxy group substituted at the 2',3'-position, and $R_1$ and $R_2$ are selected from the group consisting of a linear or branched alkyl having 1–4 carbon atoms, a methoxyethyl, or a 2-pyridyl methyl group. The compounds of the present invention are useful in relaxing cardiac or smooth muscle.

25 Claims, No Drawings

CALCIUM ANTAGONIST

BACKGROUND OF THE INVENTION

This is a continuation of co-pending application Ser. No. 716,669 filed on Mar. 27, 1985, abandoned.

The present invention relates to a novel series of compounds with potent calcium antagonist properties, useful for treatment of hypertension, angina pectoris and other cardiovascular diseases. Compounds described in the present invention are chemically related to the calcium channel blockers of the 1,4-dihydropyridine group and show a relaxing effect on the cardiac and vascular smooth muscle.

Calcium channel blockers are a very important family of compounds with different chemical structures, useful in the treatment of cardiovascular diseases. Dihydropyridines are a new class of calcium antagonists with smooth muscle relaxing properties, nifedipine (Figure 1) being the most representative, already in use in many countries as an antihypertensive and antianginal agent, and nitrendipine (Figure 2) under development at present, being a promising antihypertensive agent.

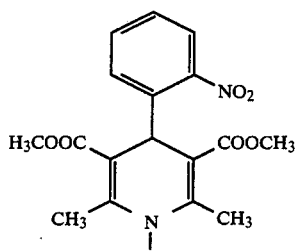

FIG. 1

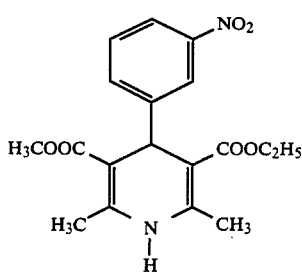

FIG. 2

The present invention relates to new 1,4-dihydropyridines with potent activity as antianginal, antihypertensive and vasodilator drugs. This invention describes some 4-(substituted phenyl)-1,4-dihydropyridines with the general formula displayed in Figure 3.

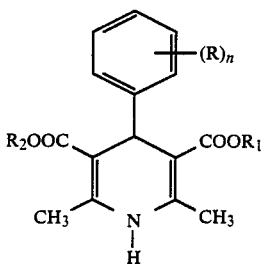

FIG. 3

SUMMARY OF THE INVENTION

The present invention relates to compounds of formula (I):

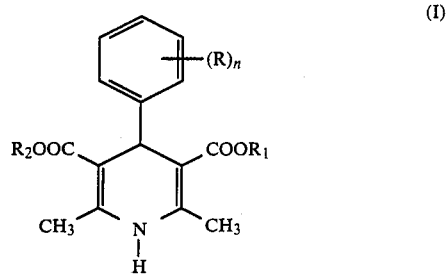

(I)

wherein:

R is preferably a hydroxy group, a $C_1$–$C_4$ linear or branched, unsubstituted or substituted alkoxy group, such as a methoxy or methoxymethoxy group, or two adjacent R groups joined together to form an alkylene dioxy group such as methylenedioxy or ethylenedioxy group;

n is preferably 1, 2, or 3;

$R_1$ and $R_2$ are preferably $C_1$–$C_4$ linear or branched, unsubstituted or substituted alkyl groups such as methyl, ethyl, propyl, isopropyl, butyl, isobutyl, methoxyethyl or 2-pyridylmethyl groups.

In the compounds of formula (I), $R_1$ and $R_2$ may be identical, giving symmetrical structures, or different and then the resulting structure shows an asymmetric center and two diastereoisomers are possible.

Among compounds of formula (I), some compounds in which the substituents in the 2 and 3 positions of the phenyl ring are joined together to form a methylenedioxy or ethylenedioxy group (more particularly compounds IQB-837 V and IQB-838 V as shown herein under, and especially compound IQB-837 V), were found very active both in "in vitro" and "in vivo" tests.

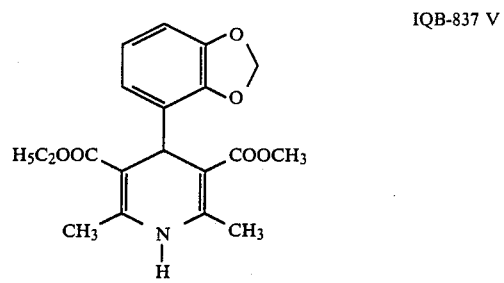

IQB-837 V

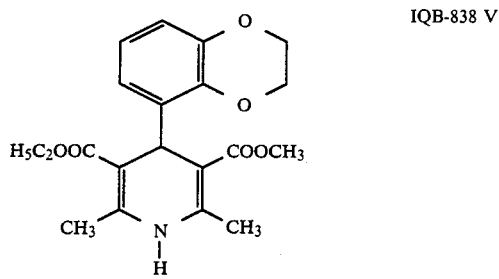

IQB-838 V

The present invention concerns also a process for preparing compounds of formula (I). That process consists in treating a substituted benzaldehyde of formula (II):

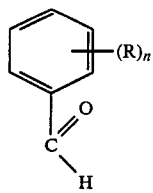
(II)

wherein R is defined as above, with an acetoacetic acid ester of formula (III):

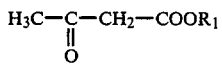
(III)

wherein $R_1$ is defined as above, then treating the resulting α-acetyl-β-(substituted phenyl)-acrylic acid ester of formula (IV):

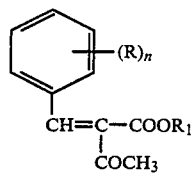
(IV)

with a 3-amino crotonic acid ester of formula (V):

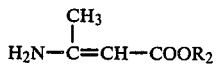
(V)

wherein $R_2$ is defined as above.

The present invention further relates to pharmaceutically acceptable preparations of compounds of formula (I) which may be administered orally, rectally, nasally, sublingually or by injection.

DETAILED DESCRIPTION OF THE PREFERRED EMBODIMENTS

Pharmaceutical Preparations

The pharmaceutical preparations are mixtures of the active ingredient, in the form of a pharmaceutically acceptable salt thereof, in association with a pharmaceutically suitable carrier. The carrier may be a solid, semi-solid or liquid diluent or an ingestible capsule. Usually, the active ingredient will compose between 0.1% and 99% by weight of the preparation, for example 0.5–10% for preparations intended for injection and between 10 and 80% for preparations intended for oral administration.

To produce pharmaceutical preparations containing a compound of the invention for oral application, the active component may be mixed with a solid, pulverulent carrier, for example lactose, saccharose, sorbitol, etc., a starch, such as corn starch, amylopectin, agar, etc., a cellulose derivative, polyvinylpyrrolidone or gelatin, and lubricants, such as magnesium or calcium stearate, Carbowax or other polyethylene glycol waxes, may be included and compressed to form tablets or cores for pills. If pills are required, the cores may be coated, for example with concentrated sugar solutions which may contain acacia gum, talc and/or titanium dioxide, or alternatively, with a film forming agent dissolved in a volatile organic solvent. Dye-stuffs can be added to these coatings, for example, to distinguish between different contents of active substance. For the preparation of soft gelatin capsules, the active substance may be dissolved in a suitable oil such as olive oil, sesame oil or arachis oil. Hard gelatin capsules may contain granulates to the active substance with solid pulverulent carriers such as lactose, saccharose, starches, cellulose derivatives, polyvinylpyrrolidone or gelatin and may also include magnesium stearate or stearic acid as lubricants.

A compound of the invention may also be formulated as a sustained release or sustained action dosage form using suitable excipients. Different methods may be used for the availability control, e.g. coated microgranules or particles, matrix imbedded drug or slightly soluble forms.

Liquid preparations for oral application may be in the form of elixirs, syrups or suspensions, for example solutions containing from about 0.1% to 10% by weight of active substance, sugar and a mixture of alcohol, water, glycerol, propylene glycol and optionally aroma, saccarine and/or carboxymethylcellulose or pectin as a dispersing agent.

For parenteral application some compounds of the invention able to form salts with acids such as hydrochloric, phosphoric, tartaric, or other organic or inorganic acids, may be prepared in aqueous solutions of the active substance. The concentration of the active substance is preferably 0.1–0.5%. A stabilizing agent and/or buffer substances may be added. Dosage units of the solution may be advantageously enclosed in ampullae or vials.

The dosage at which the active ingredients are administered may vary within a certain range and will depend on various factors, such as for example, the individual requirements of each patient. A suitable oral dosage range is from 10 to 50 mg given 1–3 times a day. A suitable dosage range for parenteral administration is from 1 to 10 mg.

Synthesis of Compounds of the Invention

Example No. 1

Preparation of 1,4-dihydro-2,6-dimethyl-4-(3',4',5'-trimethoxyphenyl)-3,5-pyridinedicarboxylic acid, methyl ethyl ester (IQB-831-v)

(a) Preparation of ethyl α-acetyl-β-(3,4,5-trimethoxyphenyl)-acrylate.

To a solution of 19.6 g. (0.11 mol) of trimethoxybenzaldehyde and 7 ml. of benzene were added 13 g. (0.1 mol) of ethyl acetoacetate in a flask connected to a Dean-Stark separator containing 100 ml. of benzene. The solution was stirred at 60°–70° C. until complete solubilization of the mixture, and then 0.4 ml. of piperidine and 1.2 ml. of acetic acid were added. The reaction mixture was refluxed for 2–3 hours until no more separation of water was observed. After cooling, white crystalline solid was filtered off, yielding 11 g. The filtrate was diluted with ether, washed with 50 ml. of 5% HCl, 50 ml. of 5% sodium bicarbonate and 50 ml. of water. The organic layer was dried over anhydrous magnesium sulfate, filtered off and evaporated under vacuum, yielding an additional 13 g. fraction. Both fractions were recrystallized from ethanol. Yield: 75%, m.p.=113.4° C.

(b) Preparation of 1,4-dihydro-2,6-dimethyl-4-(3',4',5'-trimethoxyphenyl)-3,5-pyridinedicarboxylic acid, methyl ethyl ester.

8 g. of ethyl α-acetyl-β-(3,4,5-trimethoxyphenyl)-acrylate were dissolved in 50 ml. of isopropanol, heating the mixture gently, and 2.98 g. of methyl aminocrotonate were added. The mixture was stirred at room temperature for 48 hours and the solid obtained was filtered off. The filtrate was then evaporated under vacuum yielding an oily semi-solid which was recrystallized from methanol. Yield: 5 g. (50%), m.p. 186° C.

Example No. 2

Preparation of 1,4-dihydro-2,6-dimethyl-4-(3',4'-dimethoxyphenyl)-3,5-pyridinedicarboxylic acid, methyl ether ester. (IQB-834 V).

(a) Preparation of ethyl α-acetyl-β-(3,4-dimethoxyphenyl)-acrylate.

In a round-bottom flask connected to a Dean-Stark separator containing anhydrous benzene were poured 4.1 g. (0.025 mol) of 3,4-dimethoxybenzaldehyde and 3.25 g. (0.025 mol) of ethyl acetoacetate in 5 ml. of anhydrous benzene. The mixture was heated until total solubilization, and then 0.1 ml. of piperidine and 0.3 ml. of glacial acetic acid were added. The mixture was refluxed for 2 hours until no more separation of water was observed. After cooling, the mixture was diluted with benzene and washed twice with 25 ml. of 5% HCl, 25 ml. of 5% sodium bicarbonate and water. The organic layer was dried over anhydrous magnesium sulfate and evaporated under vacuum yielding a yellow oil which was used without any further purification for the next step. Yield, 5.8 g. (85%).

(b) Preparation of 1,4-dihydro-2,6-dimethyl-4-(3',4'-dimethoxyphenyl)-3,5-pyridinedicarboxylic acid, methyl ethyl ester. 4.8 g. of ethyl α-acetyl-β-(3,4-dimethoxyphenyl)-acrylate were dissolved in 25 ml. of isopropanol and 2 g. of methyl aminocrotonate were then added. After stirring the mixture for 48 hours at room temperature, solvent was removed under vacuum giving an oily product which was recrystallized from ethanol. Yield, 5 g. (77%), m.p.=169° C.

Example No. 3

Preparation of 1,4-dihydro-2,6-dimethyl-4-(3',5'-dimethoxy-4'-hydroxyphenyl)-3,5-pyridinedicarboxylic acid, methyl ethyl ester. (IQB-832 V)

(a) Preparation of ethyl α-acetyl-β-(3,5-dimethoxy-4-hydroxyphenyl)-acrylate.

9.1 g. (0.05 mol) of 3,5-dimethoxy-4-hydroxybenzaldehyde, 6.5 g. (0.05 mol) of ethyl acetoacetate and 5 ml. of benzene were poured into a round-bottom flask connected to a Dean-Stark separator containing dried benzene. The mixture was heated until complete solubilization, and then 0.2 ml. of piperidine and 0.7 ml. of glacial acetic acid were added. The solution was refluxed for 2 hours. After cooling, a white crystalline solid precipitated from the reaction mixture. This solid was filtered off and recrystallized from ethanol. Yield, 11 g. (75%).

(b) Preparation of 1,4-dihydro-2,6-dimethyl-4-(3',5'-dimethoxy-4'-hydroxyphenyl)-3,5-pyridinedicarboxylic acid, methyl ethyl ester.

11 g. of ethyl α-acetyl-β-(3,5-dimethoxy-4-hydroxyphenyl)-acrylate were dissolved in 100 ml. of isopropanol, and 3.9 g. of methyl aminocrotonate were then added. The mixture was stirred for 48 hours at room temperature. The solvent was evaporated under vacuum yielding a yellow oil which was washed with 3×15 ml. of n-hexane. The resulting solid was recrystallized from isopropanol. Yield, 8 g. (55%) of a white crystalline solid, m.p. 186° C.

Example No. 4

Preparation of 1,4-dihydro-2,6-dimethyl-4-(2',3'-dimethoxyphenyl)-3,5-pyridinedicarboxylic acid, ethyl methyl ester. (IQB-835 V)

(a) Preparation of ethyl α-acetyl-β-(2,3-dimethoxyphenyl)-acrylate.

In a 1-l. round-bottomed flask fitted with a water-benzene separator and a reflux condenser are placed 183 g. (1.1 moles) of 2,3-dimethoxybenzaldehyde and 130 g. (1.0 mole) of ethyl acetoacetate. The water-benzene separator is filled with benzene, an additional 70 ml. of benzene is added to the mixture, and the 2,3-dimethoxybenzaldehyde is brought into solution by warming. Piperidine (4 ml.) and glacial acetic acid (12 ml.) are added, and the mixture is heated under reflux for 2-3 hours. The mixture is cooled, poured into a separatory funnel with 800 ml. of ether, and washed successively with 200 ml. portions of 5% HCl, 5% sodium bicarbonate solution, and 5% acetic acid, and twice with water. The extract is dried over anhydrous magnesium sulfate (about 250 g.). After filtration, the ether and benzene are distilled under atmospheric pressure, and the residue is distilled under reduced pressure. The yield of viscous, yellow oil collected at 186°-190°/2 mm Hg is 180-199 g. (64-72%).

The synthesis of this intermediate is described in *Organic Syntheses,* Coll. Vol. IV, pg. 408, hereby incorporated by reference.

(b) Preparation of 1,4-dihydro-2,6-dimethyl-4-(2',3'-dimethoxyphenyl)-3,5-pyridinedicarboxylic acid, ethyl methyl ester.

14 g. of ethyl α-acetyl-β-(2,3-dimethoxyphenyl) acrylate were dissolved in 50 ml. of isopropanol and 5.8 g. of methyl aminocrotonate were then added. The mixture was stirred for 48 h. at room temperature, yielding a crystalline solid which was filtered off. After removal of solvent under vacuum another fraction of product was obtained. Both portions were recrystallized from isopropanol. Yield, 11.5 g. (61%), m.p.=175° C.

Example No. 5

Preparation of 1,4-dihydro-2,6-dimethyl-4-(3',5'-dimethoxyphenyl)-3,5-pyridinedicarboxylic acid, ethyl methyl ester. (IQB-833 V)

(a) Preparation of ethyl α-acetyl-β-(3,5-dimethoxyphenyl)-acrylate.

4.1 g. of 3,5-dimethoxybenzaldehyde and 3.25 g. of ethyl acetoacetate in 5 ml. of dried benzene were poured into a round bottom flask connected to a Dean-Stark separator containing benzene. The mixture was gently heated until total solubilization and then 0.1 ml. of piperidine and 0.3 ml. of glacial acetic acid were added. The resulting solution was refluxed for 2 hours until no more separation of water was observed. After cooling, a crystalline solid precipitated. The solid was filtered off and the filtrate was washed twice with 5% HCl, 5% bicarbonate and water. The solvent was removed under vacuum yielding an oily semi-solid which was recrystallized from ethanol. Total yield, 3.8 g. (55%), m.p.=73°-75° C.

(b) Preparation of 1,4-dihydro-2,6-dimethyl-4-(3',5'-dimethoxyphenyl)-3,5-pyridinedicarboxylic acid ethyl methyl ester.

3.5 g. of ethyl α-acetyl-β-(3,5-dimethoxyphenyl)-acrylate were dissolved in 50 ml. of hot isopropanol, and 2.25 g. of methyl aminocrotonate were then added. The mixture was heated for 48 h. at 40° C. The solvent was removed under vacuum and the resulting yellow oil was boiled with n-hexane. On cooling a crystalline solid precipitated. Yield, 4 g. (85%), m.p.=122° C.

Example No. 6

Preparation of 1,4-dihydro-2,6-dimethyl-4-(2'-methoxymethoxy-phenyl)-3,5-pyridinedicarboxylic acid, ethyl methyl ester. (IQB-836 V)

(a) Preparation of 2-methoxymethoxy-benzaldehyde.

36.6 g. (0.3 mol) of salicylic aldehyde and 7.3 g. of sodium were dissolved in a mixture of 72 ml. of dried toluene and 18 ml. of absolute ethanol. To dissolve the voluminous yellow solid of the corresponding sodium salt which precipitated, 100 additional ml of toluene were added and the mixture was stirred for 1 hour. After cooling the mixture in an ice-salt bath, 24.7 g. of recently distilled monochloromethyl ether were added slowly and with vigorous stirring. The mixture was subsequently stirred for 24 h. at room temperature, the progress of reaction being evident by the formation of a white precipitate of NaCl.

The NaCl was filtered off and the filtrate was washed several times with diluted NaOH to remove the remaining salicylic aldehyde. After washing with water, the filtrate was dried over anhydrous magnesium sulfate and the solvent was evaporated under vacuum, yielding a yellow-white oil which was used without any further purification for the next step. Yield, 23 g. (46%).

(b) Preparation of ethyl α-acetyl-β-(2-methoxymethoxy-phenyl)-acrylate.

In a round bottom flask connected to a Dean-Stark separator containing benzene, 23 g. of 2-methoxymethoxy-benzaldehyde and 18 g. of ethyl acetoacetate were poured with 10 ml. of dried benzene. The mixture was heated until complete dissolution and then 0.55 ml. of piperidine and 1.6 ml. of glacial acetic acid were added. The solution was subsequently refluxed for 2 hours until no more separation of water was observed.

After cooling, the mixture was diluted with diethyl ether and washed with 100 ml. of 5% HCl, 100 ml. of sodium bicarbonate and water. The organic layer was dried over anhydrous magnesium sulfate and solvent was removed under vacuum yielding a brown oil which was purified by distillation at 2 mm Hg using for the next step the 135°-145° C. fraction. Yield, 21 g. (55%).

(c) Preparation of 1,4-dihydro-2,6-dimethyl-4-(2'-methoxymethoxy-phenyl)-3,5-pyridinedicarboxylic acid, ethyl methyl ester.

21 g. of ethyl α-acetyl-β-(2-methoxymethoxy-phenyl)-acrylate were dissolved in 50 ml. of isopropanol and after adding 8.6 g. of methylaminocrotonate, the mixture was stirred 48 hours at room temperature. The solvent was evaporated under vacuum yielding a yellow oil which was crystallized from diisopropyl ether. This product was further purified by recrystallization from ethyl acetate-cyclohexane (10:90). Yield, 17 g. (60%), m.p.=129.6° C.

Example No. 7

Preparation of 1,4-dihydro-2,6-dimethyl-4-(2',3'-methylenedioxyphenyl)-3,5-pyridinedicarboxylic acid, ethyl methyl ester (IQB-837-V).

(a) Preparation of 2,3-methylenedioxybenzaldehyde.

69 g. of 2,3-dihydroxybenzaldehyde (0.5 mol) were dissolved in 825 ml. of dimethylformamide, giving a dark solution to which were added 144.9 g. of potassium fluoride. The mixture was cooled in an ice bath and 96 g. of dibromomethane were added slowly and with vigorous stirring. The mixture was subsequently heated at 110°-120° C. for 2 hours. After cooling, the black solution was filtered through a glass filter. The cake in the filter was washed with 300 ml. of chloroform. The solvents were then removed under vacuum giving a black oil which was distilled under reduced pressure (5 mm Hg), yielding 54.5 g. (73%) of a viscous clear oil (b.p. 109° C., 5 mm Hg) which solidified slowly on standing.

(b) Preparation of ethyl α-acetyl-β-(2,3-methylenedioxyphenyl)-acrylate.
Method 1.

In a round-bottom flask connected to a Dean-Stark separator were poured 36 g. of 2,3-methylenedioxybenzaldehyde and 31.2 g. of ethyl acetoacetate in 17 ml. of benzene. The mixture was heated at 60°-70° C. and then were added 0.96 ml. of piperidine and 3.84 ml. of glacial acetic acid. The resulting clear solution was refluxed subsequently for 2 hours until no more separation of water was observed.

The solvent was removed under vacuum yielding a yellow oil which solidified on standing and which was recrystallized from ethanol. Yield 55 g. (85%), m.p.=97°-100° C.

Method 2.

5 g. of 2,3-methylenedioxybenzaldehyde, 4.5 g. of ethyl acetoacetate, 0.13 ml. of piperidine and 0.39 ml. of glacial acetic acid were dissolved in 50 ml. of absolute ethanol. The mixture was refluxed for 2 hours and the solvent was evaporated almost to dryness. After adding 50 ml. more of ethanol, the mixture was refluxed for 2 additional hours. The solvent was removed under vacuum and the resulting yellow oil solidified on standing at 4° C. and was recrystallized from ethanol. Yield, 7.3 g (83%), m.p.=97°-100° C.

(c) Preparation of 1,4-dihydro-2,6-dimethyl-4-(2',3'-methylenedioxyphenyl)-3,5-pyridinedicarboxylic acid, methyl ethyl ester.

56 g. of ethyl α-acetyl-β-(2,3-methylenedioxyphenyl)-acrylate were dissolved in 250 ml. of hot isopropanol and then were added 24 g. of dimethyl aminocrotonate. The mixture was stirred for 48 hours at 40° C. and solvent was subsequently removed under vacuum giving a white-yellow crystalline solid which was washed with diisopropyl ether. The crude was then recrystallized twice from ethanol. Yield 55 g. (72%), m.p.=166.5° C.

Example No. 8

Preparation of 1,4-dihydro-2,6-dimethyl-4-(2',3'-ethylenedioxyphenyl)-3,5-pyridinedicarboxylic acid, methyl ethyl ester (IQB-838-V).

(a) Preparation of 2,3-ethylenedioxybenzaldehyde.

5.52 g (0.04 mol) of 2,3-dihydroxybenzaldehyde were dissolved in 75 ml. of dimethylformamide giving a black solution to which was added 11.6 g. of potassium fluoride. The mixture was cooled in an ice bath and 7.5 g. of 1,2-dibromoethane were added slowly with vigorous stirring. The mixture was subsequently heated for 2 hours at 110°-120° C. giving a black solution. After cooling, this solution was filtered through a glass filter. The remaining inorganic solid in the filter was washed with chloroform to remove any organic product. The filtrates were diluted with 100 ml. of water and were extracted with chloroform. The organic layer was then decanted, washed with 1N sodium hydroxide and water, dried over anhydrous magnesium sulfate and evaporated under vacuum to yield a viscous oil which was used without any further purification for the next step. Yield, 4.5 g. (70%).

(b) Preparation of ethyl α-acetyl-β-(2,3-ethylenedioxyphenyl)-acrylate.

In a round-bottom flask connected to a Dean-Stark separator containing dried benzene were poured 4.5 g. of 2,3-ethylenedioxybenzaldehyde, 3.5 g. of ethyl acetoacetate and 10 ml. of benzene. The mixture was gently heated until complete dissolution and 0.12 ml. of piperidine and 0.4 ml. of glacial acetic acid were subsequently added. The resulting solution was refluxed for 2 hours until reaction was completed.

After cooling, the mixture was diluted with benzene and washed with 3×25 ml. of 5% HCl, 5% sodium bicarbonate and water. The organic layer was decanted, dried over anhydrous magnesium sulfate and the solvent was evaporated under vacuum yielding a viscous oil which solidified slowly on standing and which was recrystallized from ethanol. Yield, 6.5 g. (85%).

(c) Preparation of 1,4-dihydro-2,6-dimethyl-4-(2',3'-ethylenedioxyphenyl)-3,5-pyridinedicarboxylic acid, methyl ethyl ester.

6.5 g. of ethyl α-acetyl-β-(2,3-ethylenedioxyphenyl)-acrylate were dissolved in 50 ml. of hot isopropanol and 2.7 g. of methyl aminocrotonate were then added. The mixture was stirred for 48 hours at 40° C. and the solvent was subsequently removed under vacuum, yielding a yellow oil which was recrystallized from ethanol. Yield, 6.8 g. (77%), m.p.=169° C.

Example No. 9

Preparation of 1,4-dihydro-2,6-dimethyl-4-(2',3'-methylenedioxyphenyl)-3,5-pyridinedicarboxylic acid, dimethyl ester (IQB-841).

(a) Preparation of methyl α-acetyl-β-(2,3-methylenedioxyphenyl)-acrylate.

In a round-bottom flask connected to a Dean-Stark separator were poured 28 g. of 2,3-methylenedioxybenzaldehyde and 21.6 g. of methyl acetoacetate in 13 ml. of dried benzene. The mixture was heated until dissolved and then were added 0.74 ml. of piperidine and 2.24 ml. of glacial acetic acid. The resulting solution was refluxed for 2 hours until no more release of water was observed.

After cooling, the mixture was diluted with benzene, washed with 20 ml. of 5% HCl, 5% sodium bicarbonate and water. The organic layer was decanted, dried over anhydrous magnesium sulfate and evaporated under vacuum, yielding a yellow oil which was used directly for the next step. Yield, 25 g. (54%). A sample of oil was purified by recrystallization from ethanol 90° C. giving a yellow-white solid, m.p.=73°-74° C.

(b) Preparation of 1,4-dihydro-2,6-dimethyl-4-(2',3'-methylenedioxyphenyl)-3,5-pyridinedicarboxylic acid, dimethyl ester.

10 g. of crude methyl α-acetyl-β-(2,3-methylenedioxyphenyl)-acrylate were dissolved in 50 ml. of hot isopropanol. Subsequently, 4.3 g. of methyl aminocrotonate were added. The mixture was stirred at room temperature for 48 hours. The solid which precipitated from the mixture was filtered off and the filtrate was evaporated under vacuum to yield an oil which was recrystallized twice from hot methanol. Yield, 6 g. (43%), m.p.=202° C.

Example No. 10

Preparation of 1,4-dihydro-2,6-dimethyl-4-(2',3'-methylenedioxyphenyl)-3,5-pyridinedicarboxylic acid, methyl isobutyl ester (IQB-842).

(a) Preparation of isobutyl α-acetyl-β-(2,3-methylenedioxyphenyl)-acrylate.

In a round bottom flask connected to a Dean-Stark separator containing dried benzene were poured 10 g. of 2,3-methylenedioxybenzaldehyde, 10.5 g. of isobutyl acetoacetate and 5 ml. of benzene. The mixture was heated until dissolved and then were added 0.26 ml. of piperidine and 0.80 ml. of glacial acetic acid. The resulting solution was refluxed for 2 hours until the reaction was completed. The mixture was diluted with benzene and washed with 3×20 ml of 5% HCl, 5% sodium bicarbonate and water. The organic layer was dried over anhydrous magnesium sulfate and the solvent was removed under vacuum giving an oil which crystallized on adding n-hexane. The product was purified by recrystallization from isopropanol-n-hexane. Yield, 13.3 g. (69%), m.p.=62°-64° C.

(b) Preparation of 1,4-dihydro-2,6-dimethyl-4-(2',3'-methylenedioxyphenyl)-3,5-pyridinedicarboxylic acid, methyl isobutyl ester.

10 g. of isobutyl α-acetyl-β-(2,3-methylenedioxyphenyl)-acrylate were dissolved in 50 ml. of hot isopropanol. To the hot solution were then added 4 g. of methyl aminocrotonate and the mixture was stirred for 48 h. at room temperature. The solvent was removed under vacuum and the resulting oil solidified on cooling after boiling it with n-hexane. Yield, 10 g. (80%), m.p.=153° C.

Example No. 11

Preparation of 1,4-dihydro-2,6-dimethyl-4-(2',3'-methylenedioxyphenyl)-3,5-pyridinedicarboxylic acid, isopropyl methoxyethyl ester (IQB-843).

(a) Preparation of methoxyethyl α-acetyl-β-(2,3-methylenedioxyphenyl)-acrylate.

In a round-bottom flask with a Dean-Stark separator containing dried benzene were poured 10 g. of 2,3-methylenedioxybenzaldehyde and 10.6 g. of methoxyethyl acetoacetate in 10 ml. of benzene. The mixture was heated until complete dissolution and then 0.26 ml. of piperidine and 0.78 ml. of glacial acetic acid were added. The resulting solution was refluxed for 2 hours until no more release of water was observed.

The mixture was then diluted with 25 ml. of benzene and washed with 25 ml. of 5% HCl, 25 ml. of 5% sodium bicarbonate and water. The organic layer was decanted, dried over anhydrous magnesium sulfate and evaporated under vacuum yielding a yellow oil which solidified on cooling. The product was purified by recrystallization from isopropanol. Yield 13.3 g. (69%), m.p.=87° C.

(b) Preparation of 1,4-dihydro-2,6-dimethyl-4-(2',3'-methylenedioxyphenyl)-3,5-pyridinedicarboxylic acid, isopropyl methoxyethyl ester.

3.5 g. of methoxyethyl α-acetyl-β-(2,3-methylenedioxyphenyl)-acrylate were dissolved in 25 ml. of hot isopropanol and were mixed with 1.71 g. of isopropyl aminocrotonate, stirring the resulting mixture for 48 h at 40° C. The solvent was removed under vacuum giving a yellow oil which solidified on adding n-hexane. The product was purified by recrystallization from isopropanol-n-hexane. Yield, 4 g. (80%), m.p.=129.6° C.

Example No. 12

Preparation of 1,4-dihydro-2,6-dimethyl-4-(2',3'-methylenedioxyphenyl)-3,5-pyridinedicarboxylic acid, diisopropyl ester (IQB-844).

(a) Preparation of isopropyl α-acetyl-β-(2,3-methylenedioxyphenyl)-acrylate.

In a round-bottom flask connected to a Dean-Stark separator containing benzene were poured 5 g. of 2,3-methylenedioxybenzaldehyde, 4.8 g. of isopropyl acetoacetate and 4 ml. of dried benzene. The mixture was heated until dissolved and then 0.13 ml. of piperidine and 0.39 ml. of glacial acetic acid were added. The resulting solution was refluxed for 2 hours until no more separation of water was observed. After cooling, the mixture was dissolved in benzene, washed with 20 ml. of 5% HCl, 20 ml. of sodium bicarbonate and water. The organic layer was decanted, dried over anhydrous magnesium sulfate and evaporated under vacuum giving a solid substance which was recrystallized from n-hexane-isopropanol. Yield, 7 g. (77%), m.p.=88° C.

(b) Preparation of 1,4-dihydro-2,6-dimethyl-4-(2',3'-methylenedioxyphenyl)-3,5-pyridinedicarboxylic acid, diisopropyl ester.

5 g. of isopropyl α-acetyl-β-(2,3-methylenedioxyphenyl)-acrylate were dissolved in 50 ml. of hot isopropanol. 2.5 g of isopropyl aminocrotonate were added, and the resulting solution was stirred for 48 h. at 40° C. The solvent was evaporated under vacuum giving an oil which solidified on standing and which was recrystallized from n-hexane-isopropanol. Yield 3.5 g. (48%), m.p.=158° C.

Example No. 13

Preparation of 1,4-dihydro-2,6-dimethyl-4-(2',3'-methylenedioxyphenyl)-3,5-pyridinedicarboxylic acid, methyl isopropyl ester (IQB-845).

(a) Preparation of methyl α-acetyl-β-(2,3-methylenedioxyphenyl)-acrylate.

This intermediate was prepared according to the method described in example 9.

(b) Preparation of 1,4-dihydro-2,6-dimethyl-4-(2',3'-methylenedioxyphenyl)-3,5-pyridinedicarboxylic acid, methyl isopropyl ester.

5 g. of methyl α-acetyl-β-(2,3-methylenedioxyphenyl)-acrylate were dissolved in 30 ml. of hot isopropanol and then 2.8 g. of isopropyl aminocrotonate were added. The mixture was subsequently stirred for 48 h at room temperature. The solvent was removed under vacuum yielding an oil which solidified after adding n-hexane. The product was purified by recrystallization from n-hexane-isopropanol. Yield, 3 g. (40%).

Example No. 14

Preparation of 1,4-dihydro-2,6-dimethyl-4-(2',3'-methylenedioxyphenyl)-3,5-pyridinedicarboxylic acid, diethyl ester (IQB-846).

(a) Preparation of ethyl α-acetyl-β-(2,3-methylenedioxyphenyl)-acrylate.

This intermediate was prepared as described in example 7.

(b) Preparation of 1,4-dihydro-2,6-dimethyl-4-(2',3'-methylenedioxyphenyl)-3,5-pyridinedicarboxylic acid, diethyl ester.

5 g. (0.019 mol) of ethyl α-acetyl-β-(2,3-methylenedioxyphenyl)acrylate were dissolved in 35 ml of isopropanol at 40° C. and then 2.45 g. (0.019 mol) of ethyl 3-aminocrotonate were added. The mixture was stirred for 48 h. at 40° C. After cooling, n-hexane was added until the solution became cloudy. After filtering, the filtrate was cooled overnight at 4° C. The solid which precipitated was filtered off and dried. Yield, 3.66 g. (51%), m.p.=173° C.

Example No. 15

Preparation of 1,4-dihydro-2,6-dimethyl-4-(2',3'-methylenedioxyphenyl)-3,5-pyridinedicarboxylic acid, ethyl isopropyl ester (IQB-847).

(a) Preparation of ethyl α-acetyl-β-(2,3-methylenedioxyphenyl)-acrylate.

This compound was prepared as described in example 7.

(b) Preparation of 1,4-dihydro-2,6-dimethyl-4-(2',3'-methylenedioxyphenyl)-3,5-pyridinedicarboxylic acid, ethyl isopropyl ester.

5 g. of ethyl α-acetyl-β-(2,3-methylenedioxyphenyl)-acrylate were dissolved in 50 ml. of not isopropanol and then 2.66 g. of isopropyl aminocrotonate were added. The mixture was heated for 48 h. at 40° C. The solvent was removed under vacuum giving a solid which was recrystallized from n-hexane. Yield, 4.5 g. (62%), m.p.=165° C.

Example No. 16

Preparation of 1,4-dihydro-2,6-dimethyl-4-(2',3'-methylenedioxyphenyl)-3,5-pyridinedicarboxylic acid, dimethoxyethyl ester (IQB-848).

(a) Preparation of methoxyethyl α-acetyl-β-(2,3-methylenedioxyphenyl)-acrylate.

This compound was prepared as described in example 11.

(b) Preparation of 1,4-dihydro-2,6-dimethyl-4-(2',3'-methylenedioxyphenyl)-3,5-pyridinedicarboxylic acid, dimethoxyethyl ester.

4 g. of methoxyethyl α-acetyl-β-(2,3-methylenedioxyphenyl)-acrylate were dissolved in 15 ml. of hot isopropanol and then 1.6 g. of methoxyethyl aminocrotonate were added. The mixture was stirred at 40° C. for 48 hours. The solvent was evaporated under vacuum giving a yellow oil which solidified on cooling. The product was recrystallized from a mixture of n-hexane-isopropanol. Yield, 3.5 g. (59%), m.p.=145° C.

Example No. 17

Preparation of 1,4-dihydro-2,6-dimethyl-4-(2',3'-methylenedioxyphenyl)-3,5-pyridinedicarboxylic acid, methyl, 2-pyridylmethyl ester, hydrochloride (IQB-849).

(a) Preparation of 2-pyridylmethyl-3-aminocrotonate.

In a 100 ml round-bottom flask were poured 10 g. (0.091 mol) of 2-hydroxymethylpyridine. The flask was heated at 80°-85° C. and 37 mg. of recently melted sodium acetate were added. When the solution was stirred vigorously, and the temperature maintained below 120° C., 7.64 g. (7 ml., 0.091 mol) of diketene were dropped. The mixture was subsequently heated for 2 hours at 80°-90° C. After cooling, the mixture was distilled under vacuum (1 mm. Hg) collecting the fraction of 2-pyridylmethyl acetoacetate which distilled at 110° C. The collected distillate was diluted with 5 ml. of methanol, cooled in an ice bath and bubbled with an ammonia stream for 3 hours, yielding a yellow solid which was filtered, dried and recrystallized from n-hexane. Yield, 1.92 g. (11%), m.p.=93° C.

(b) Preparation of methyl α-acetyl-β-(2,3-methylenedioxyphenyl)-acrylate.

This compound is prepared as described in example 9.

(c) Preparation of 1,4-dihydro-2,6-dimethyl-4-(2',3'-methylenedioxyphenyl)-3,5-pyridinedicarboxylic acid, methyl, 2-pyridylmethyl ester.

2.39 g. (9.6 mmol) of methyl α-acetyl-β-(2,3-methylenedioxyphenyl)-acrylate were dissolved in 18 ml. of hot isopropanol and then 1.86 g. (9.6 mmol) of 2-pyridylmethyl aminocrotonate were added, and the mixture was stirred for 2 days at 40° C. The solvent was subsequently removed under vacuum and the residual solid was dissolved in 2 ml. of ethanol 96% adding a few drops of n-hexane. The mixture was cooled overnight at 4° C. giving 3 g. (74%) of a white crystalline powder, m.p.=161°-162° C.

(d) 1,4-dihydro-2,6-dimethyl-4-(2',3'-methylenedioxyphenyl)-3,5-pyridinedicarboxylic acid, methyl, 2-pyridylmethyl ester, hydrochloride.

1.4 g. of base obtained as described above were dissolved in 20 ml. of hot isopropanol. After cooling, a solution of HCl in isopropanol was dropped until pH near to 2. On standing, a white crystalline solid precipitated. Yield, 1.44 g. (95%), m.p.=134°-136° C. (with decomposition).

Pharmacology

The compounds of the present invention were tested in their calcium channel blocking properties by "in vitro" and "in vivo" standard methods.

1. "In vitro" tests

Inhibitory effects on rat aorta contractions induced by KCl:

Wistar rats (220-250 g. were killed by decapitation and aortas were removed and placed in a 20 ml. bath at 34° C., containing Krebs medium of the following composition in mmol/l.: NaCl:137; KCl:2.7; $MgCl_2.6H_2O$:1.04; $CaCl_2.2H_2O$:0.8; $Na_2HPO_4.H_2O$:0.42; $NaHCO_3$:11.9; glucose:5; oxygenated with 95% $O_2$+5% $CO_2$ (Furchgott & Bhadakrom, 1956). After a 45 minute stabilization period under 2 g. tension, maximal contractions of artery were induced by adding KCl to the bath to give a final concentration of 80 mmol./l. After the contractions had stabilized, the compounds of the present invention or nifedipine which was used as positive control, were added cumulatively, allowing at least 10 minutes between additions for stabilization of relaxation. The compounds of the present invention were dissolved in ethanol to give stock solutions of about 1 mg./ml. from which were obtained work dilutions from $10^{-10}$M to $10^{-6}$M by adding normal saline. 50% inhibitory concentrations (IC 50) were determined by regression analysis.

2. "In vivo" tests

The systolic blood pressure was measured on the tail of conscious, spontaneously hypertensive rats (SHR), by means of an inflatable rubber cuff and a Digital Pressure meter LE 5000 (Letica Instruments, Barcelone, Spain). Measurements were carried out before administration of the substance, as well as 30 minutes, 1 h, 2, 6, and 24 hours afterwards, respectively. The animals were kept in pre-warmed plastic cylinders during the measurements. The rats with a blood pressure lesser than 160 mm. Hg were discarded. Each compound was tested in 5 animals. Compounds of this invention, or nitrendipine which was used as positive control were given orally in the form of suspensions in 5% acacia gum.

Table 1 shows the in vitro activity of the compounds of this invention on rat aorta contractions induced by KCl 80 mM. It can be seen that compound 7 was the most active within the series of methyl ethyl ester derivatives with a value of IC 50=3.5·$10^{-9}$M.

In the same test, IC 50 of nifedipine was 7.5·$10^{-9}$M about two times less active than compound 7. Compounds 1, 2 and 3, with a substituent in the para position of the phenyl group, were found to have little or no activity. Compound 6, with an ortho-methoxymethoxy group showed a rather than activity as did compound 8. In the group of derivatives of compound 7, the better activity was seen in asymmetrical compounds. This characteristic is common to all 1,4-dihydropyridine calcium antagonists, symmetrical compounds being in general less active than asymmetric compounds. Compound 15 was as active as compound 7 with a value of IC 50=2.1×$10^{-9}$M.

Table 2 shows in vivo activity on blood pressure on SHR rats. In this test compound 7 (8 mg./kg. p.os) was as active as nitrendipine (8 mg./kg. p.os), decreasing blood pressure by 30% in SHR rats. Compound 8, which was rather active in vitro, exhibited a little antihypertensive effect, whereas compounds 6, 10 and 15 were also active in vivo.

TABLE 1

In vitro activity of compounds of the invention on KCl depolarized rat aorta.

| R | $R_1$ | $R_2$ | No | IQB | IC × $10^{-8}$ |
|---|---|---|---|---|---|
| 3',4',5'-trimethoxy | ethyl | methyl | 1 | 831 V | >10 |
| 3',4'-dimethoxy- | ethyl | methyl | 2 | 834 V | >10 |
| 3',5'-dimethoxy 4'-hydroxy | ethyl | methyl | 3 | 832 V | >10 |
| 2',3'-dimethoxy | ethyl | methyl | 4 | 835 V | >10 |
| 3',5'-dimethoxy | ethyl | methyl | 5 | 833 V | 9.2 |
| 2'-methoxymethoxy | ethyl | methyl | 6 | 836 V | 1.2 |
| 2',3'-methylenedioxy | ethyl | methyl | 7 | 837 V | 0.31 |
| 2',3'-ethylenedioxy | ethyl | methyl | 8 | 838 | 4.5 |
| 2',3'-methylenedioxy | methyl | methyl | 9 | 841 | 8.3 |
| 2',3'-methylenedioxy | isobutyl | methyl | 10 | 842 | 1.2 |
| 2',3'-methylenedioxy | methoxyethyl | isopropyl | 11 | 843 | 9.1 |
| 2',3'-methylenedioxy | isopropyl | isopropyl | 12 | 844 | >10 |
| 2',3'-methylenedioxy | methyl | isopropyl | 13 | 845 | 3.4 |
| 2',3'-methylenedioxy | ethyl | ethyl | 14 | 846 | >10 |
| 2',3'-methylenedioxy | ethyl | isopropyl | 15 | 847 | 0.21 |
| 2',3'-methylenedioxy | methoxyethyl | methoxyethyl | 16 | 848 | >10 |
| 2',3'-methylenedioxy | methyl | 2-pyridylmethyl | 17 | 849 | >10 |
| Nifedipine | | | | | 0.71 |

TABLE 2

Antihypertensive efficacy of compounds of the invention in SHR rats.
(Dose: 8 mg./kg. p.os., n = 5)

| | maximum decrease of blood pressure | |
|---|---|---|
| Compound | mm Hg | % |
| 1 | 9.8 | 5 |
| 6 | 34 | 15.2 |
| 7 | 65 | 33 |

TABLE 2-continued

Antihypertensive efficacy of compounds
of the invention in SHR rats.
(Dose: 8 mg./kg. p.os., n = 5)

| Compound | maximum decrease of blood pressure | |
|---|---|---|
| | mm Hg | % |
| 8 | 12 | 7.2 |
| 10 | 48 | 23.5 |
| 13 | 10 | 5.2 |
| 15 | 62 | 32.4 |
| nitrendipine | 54 | 26.3 |

What is claimed is:

1. A compound of the formula

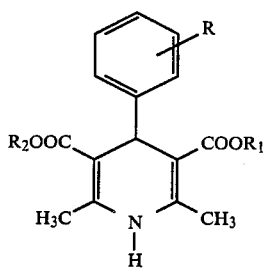

and salts thereof resulting from addition with pharmaceutically acceptable mineral or organic acid, wherein:
R is an alkylenedioxy group substituted at the 2',3'-position; and
$R_1$ and $R_2$ are selected from the group consisting of a linear or branched alkyl having 1-4 carbon atoms, a methoxyethyl, or a 2-pyridyl methyl group.

2. A compound according to claim 1 wherein $R_1$ and $R_2$ are selected from the group consisting of methyl, ethyl, propyl, isopropyl, butyl, or isobutyl groups.

3. A compound, according to claim 1, having the formula 1,4-dihydro-2,6-dimethyl-4-(2',3'-methylenedioxyphenyl)-3,5-pyridinedicarboxylic acid, methyl ethyl ester.

4. A compound, according to claim 1, having the formula 1,4-dihydro-2,6-dimethyl-4-(2',3'-ethylenedioxyphenyl)-3,5-pyridinedicarboxylic acid, methyl ethyl ester.

5. A compound, according to claim 1, having the formula 1,4-dihydro-2,6-dimethyl-4-(2',3'-methylenedioxyphenyl)-3,5-pyridinedicarboxylic acid, methyl isobutyl ester.

6. A compound, according to claim 1, having the formula 1,4-dihydro-2,6-dimethyl-4-(2',3'-methylenedioxyphenyl)-3,5-pyridinedicarboxylic acid, methyl isopropyl ester.

7. A compound, according to claim 1, having the formula 1,4-dihydro-2,6-dimethyl-4-(2',3'-methylenedioxyphenyl)-3,5-pyridinedicarboxylic acid, ethyl isopropyl ester.

8. A pharmaceutical composition comprising a smooth or cardiac muscle relaxing amount of a compound according to claim 1 together with a pharmaceutically acceptable carrier.

9. The pharmaceutical composition of claim 8 wherein said smooth or cardiac muscle relaxing amount comprises a unit dosage of about 1-50 mg of said compound.

10. A pharmaceutical composition comprising a smooth or cardiac muscle relaxing amount of a compound according to claim 3 together with a pharmaceutically acceptable carrier.

11. A pharmaceutical composition comprising a smooth or cardiac muscle relaxing amount of a compound according to claim 4 together with a pharmaceutically acceptable carrier.

12. A pharmaceutical composition comprising a smooth or cardiac muscle relaxing amount of a compound according to claim 5 together with a pharmaceutically acceptable carrier.

13. A pharmaceutical composition comprising a smooth or cardiac muscle relaxing amount of a compound according to claim 6 together with a pharmaceutically acceptable carrier.

14. A pharmaceutical composition comprising a smooth or cardiac muscle relaxing amount of a compound according to claim 7 together with a pharmaceutically acceptable carrier.

15. The pharmaceutical composition of claim 10 wherein said smooth or cardiac muscle relaxing amount comprises a unit dosage of about 1-50 mg of said compound.

16. The pharmaceutical composition of claim 11 wherein said smooth or cardiac muscle relaxing amount comprises a unit dosage of about 1-50 mg of said compound.

17. The pharmaceutical composition of claim 12 wherein said smooth or cardiac muscle relaxing amount comprises a unit dosage of about 1-50 mg of said compound.

18. The pharmaceutical composition of claim 13 wherein said smooth or cardiac muscle relaxing amount comprises a unit dosage of about 1-50 mg of said compound.

19. The pharmaceutical composition of claim 14 wherein said smooth or cardiac muscle relaxing amount comprises a unit dosage of about 1-50 mg of said compound.

20. A method of relaxing cardiac or smooth muscle comprising administering to a mammalian host a therapeutically effective amount of the compound according to claim 1.

21. A method of relaxing cardiac or smooth muscle comprising administering to a mammalian host a therapeutically effective amount of the compound according to claim 3.

22. A method of relaxing cardiac or smooth muscle comprising administering to a mammalian host a therapeutically effective amount of the compound according to claim 4.

23. A method of relaxing cardiac or smooth muscle comprising administering to a mammalian host a therapeutically effective amount of the compound according to claim 5.

24. A method of relaxing cardiac or smooth muscle comprising administering to a mammalian host a therapeutically effective amount of the compound according to claim 6.

25. A method of relaxing cardiac or smooth muscle comprising administering to a mammalian host a therapeutically effective amount of the compound according to claim 7.

* * * * *

UNITED STATES PATENT AND TRADEMARK OFFICE
CERTIFICATE OF CORRECTION

PATENT NO. : 4,722,931

DATED : February 2, 1988

INVENTOR(S) : Verde Casanova et al.

It is certified that error appears in the above-identified patent and that said Letters Patent are hereby corrected as shown below:

Col. 4, line 8, please delete "to" and insert -- of --.

Col. 5, line 36, after "ester.", please end the paragraph and begin a new paragraph.

Col. 8, line 46, please delete "dimethyl" and insert -- methyl --

Col. 12, line 21, please delete "not" and insert -- hot --.

Col. 14, line 11, please delete "than" and insert -- good --.

Signed and Sealed this

First Day of November, 1988

Attest:

DONALD J. QUIGG

Attesting Officer

Commissioner of Patents and Trademarks